US00PP32130P2

(12) United States Plant Patent
Taliaferro

(10) Patent No.: US PP32,130 P2
(45) Date of Patent: Aug. 25, 2020

(54) TURF BERMUDAGRASS 'JSC 2-21-18'

(50) Latin Name: ***Cynodon dactylon* var. *dactylon* (L.) Pers. x *Cynodon transvaalensis* Burtt-Davy**
Varietal Denomination: JSC 2-21-18

(71) Applicant: JOHNSTON SEED COMPANY, LLC, Enid, OK (US)

(72) Inventor: Charles M. Taliaferro, Stillwater, OK (US)

(73) Assignee: Johnston Seed Company, LLC, Enid, OK (US)

( * ) Notice: Subject to any disclaimer, the term of this patent is extended or adjusted under 35 U.S.C. 154(b) by 0 days.

(21) Appl. No.: 16/501,093

(22) Filed: Feb. 21, 2019

(51) Int. Cl.
*A01H 5/12* (2018.01)

(52) U.S. Cl.
USPC ..... Plt./389

(58) Field of Classification Search
USPC ..... Plt./389
CPC ..... A01H 5/12
See application file for complete search history.

(56) References Cited

PUBLICATIONS

Parsons et al. 2013 National Turfgrass Evaluation Program Bermudagrass Test: 2015 Data. Kansas Agricultural Experiment Station Research Reports vol. 2 Jul. 2016.*

* cited by examiner

*Primary Examiner* — Annette H Para
(74) *Attorney, Agent, or Firm* — Crowe & Dunlevy; Terry L. Watt

(57) ABSTRACT

'JSC 2-21-18' turf bermudagrass is disclosed as a new clonal cultivar. 'JSC 2-21-18' is an interspecific $F_1$ hybrid originating from a cross of *Cynodon dactylon* var. *dactylon* (L.) Pers. x *Cynodon transvaalensis* Burtt-Davy parent plants.

5 Drawing Sheets

SUMMARY OF THE INVENTION

'JSC 2-21-18' turf bermudagrass is disclosed as a new clonal cultivar. 'JSC 2-21-18' is an interspecific $F_1$ hybrid originating from a cross of *Cynodon dactylon* var. *dactylon* (L.) Pers. x *Cynodon transvaalensis* Burtt-Davy parent plants.

DETAILED BOTANICAL DESCRIPTION

Description, Origin and History

Figure 1:
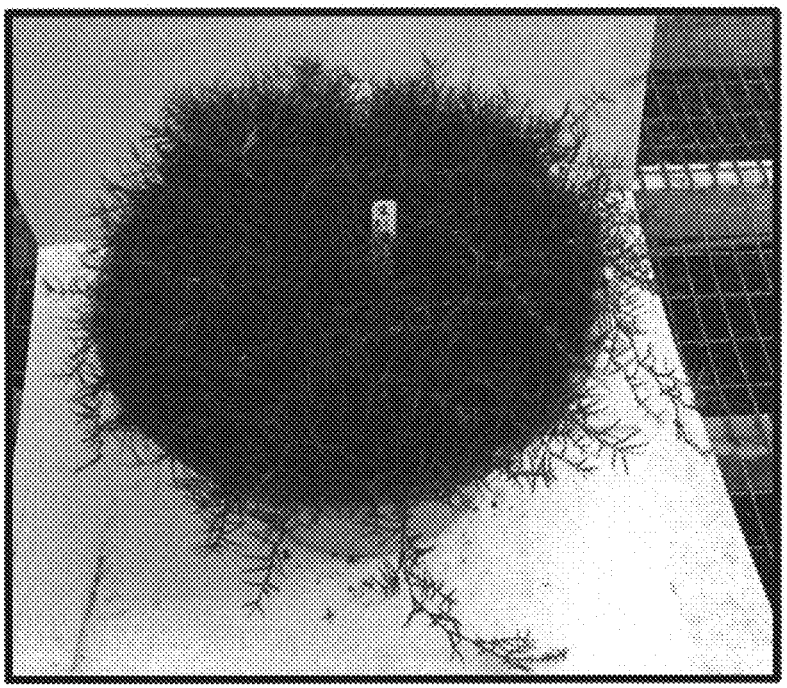
FIG. 1 is a photo of 'JSC 2-21-18' turf bermudagrass growing in a 30 cm diameter pot in the greenhouse.

'JSC 2-21-18' turf bermudagrass is a clonally propagated interspecific $F_1$ hybrid plant resulting from a cross of respective parent plants of *Cynodon dactylon* var. *dactylon* (L.) Pers. and *Cynodon transvaalensis* (Burtt-Davy). Natural crossing between plants of *Cynodon dactylon* var. *dactylon* and *Cynodon transvaalensis* is known to occur at relatively high frequency. Accordingly, interspecific crossing was achieved by growing a selected plant of *C. dactylon* ('Cda 35-5') in proximity to a selected plant of *C. transvaalensis* ('Ctr 4-10') in a small field plot (ca 9 m2) isolated from other bermudagrass. The plot was located on a Johnston Seed Company (JSC) farm near Enid, Okla. The 'Cda 35-5' and 'Ctr 4-10' plants were selected from JSC bermudagrass breeding nurseries on the bases of good adaptation, turf quality, and fertility. Seeds harvested from the small crossing block in summer 2007 were used to start individual plants in the greenhouse in late winter 2008. These plants were transplanted to a field screening nursery as spaced plants (8' centers, 2' alleys) in May 2008. The screening nursery was located on a JSC farm in Major County Okla. (36° 22' 23.99", −98° 21' 25.28") approximately 25 miles west of Enid, Okla. 'JSC 2-21-18' was selected in late 2009 for more comprehensive evaluation. It was identified at time of selection by its nursery plot ID, 2-21-18. It and other JSC experimental turf bermudagrasses were established in a replicated small plot test in May 2010 at the JSC research center at Enid, Okla. 36° 26' 13.79", −97° 48' 51.35"). This test was managed using the typical protocol used for golf course bermudagrass fairways. Entries in the test were evaluated for visual turf quality and other characteristics influencing overall performance. In January, 2013, 540 clonal plants of 'JSC 2-21-18' were started in the JSC greenhouse, Enid, Okla., in plastic trays (18 cells/tray) and subsequently shipped to the National Turfgrass Evaluation Program (NTEP) which then distributed required amounts of planting material to each of the 19 sites participating in the NTEP 2013 turf bermudagrass evaluation test. In winter 2015, clonal plants of 'JSC 2-21-18' were started in the JSC greenhouse, Enid, Okla., and subsequently used to plant a 1.24 acre scale-up nursery in summer 2015 at the JSC research center, Enid, Okla., Garfiled county (36° 26' 13.79", −97° 48' 51.35"). In July 2017, springs were taken from the 1.24 acre 'JSC 2-21-18' scale up plot and used to plant a 6.71-acre sod production field on a JSC farm near Enid, Okla. in Garfield county (36° 28' 52.97", −97° 59' 4.11").

Putative chromosome numbers of 'Cda 35-5', 'Ctr 4-10' and 'JSC 2-21-18' are respectively 2n=4x=36, 2n=2x=18, and 2n=3x=27. Accordingly, 'JSC 2-21-18' received 18 chromosomes (two genomes) from the 'Cda 35-5' parent and 9 chromosomes (one gnome) from the 'Ctr 4-10' parent. 'JSC 2-21-18' is highly sexually sterile, setting only an occasional seed when grown in the presence of one or more fertile plants of the *C. dactylon* and/or *C. transvaalensis* taxa that serve as pollinators. High sterility is typical for triploid plants with an unbalanced number of genomes. The high sexual sterility of 'JSC 2-21-18' is presumed to result from the nine chromosomes (one genome) received from the 'Ctr 4-10' parent having no fully homologous chromosomal pairing partners during meiosis. Both parents of 'JSC 2-21-18' are highly sexually fertile. The morphology and sexual sterility of 'JSC 2-21-18' are consistent with expectations for interspecific hybrids of *C. dactylon* and *C. transvaalensis*. The fidelity of 'JSC 2-21-18' has been maintained through many clonal generations of propagation since it's selection in 2008 indicating it to be genetically stable.

Figure 2:
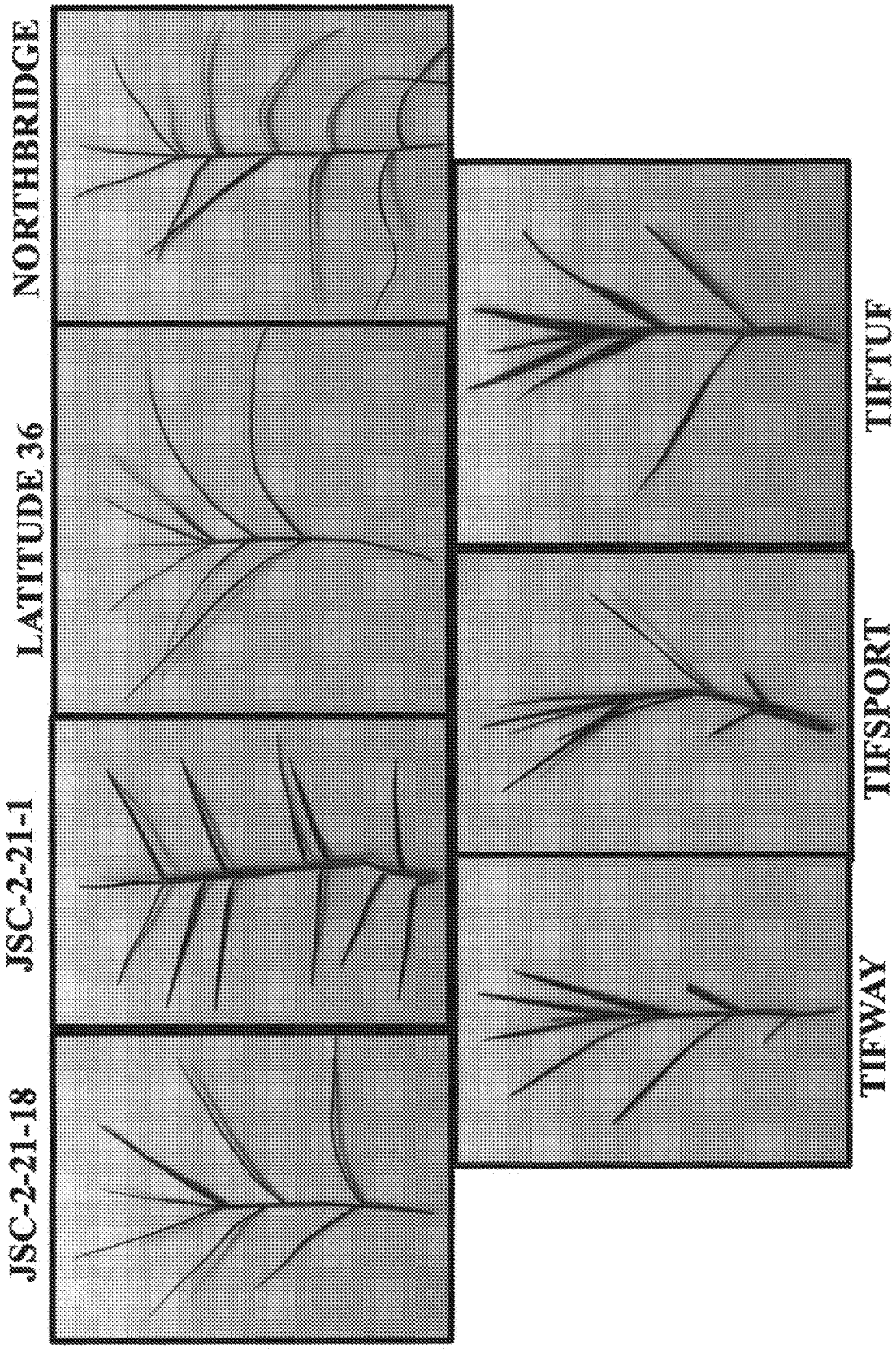
FIG. 2 shows a vegetative shoot of 'JSC 2-21-18' in comparison to vegetative shoots of other turf bermudagrass cultivars.

'JSC 2-21-18' is a stoloniferous sward-forming perennial with slender underground rhizomes. 'JSC 2-21-18' has morphological features with mean values generally between those of the parents. A plant of 'JSC 2-21-18' growing in a greenhouse pot is shown in FIG. 1. A vegetative shoot of 'JSC 2-21-18' is shown in FIG. 2 in comparison to shoots of other clonal turf bermudagrass cultivars. Shoots of 'JSC 2-21-18' are slender attaining a maximum height of approximately 25 cm on un-mowed swards. Leaf size (length and width) and stem size diameter) of JSC '2-21-18' are smaller than 'Cda 35-5' and slightly larger than 'Ctr 4-10'. Shoot density of 'JSC 2-21-18' is high resulting in a dense sward. The sod density (conditioned by shoot density) of 'JSC 2-21-18' is substantially greater than that of 'Cda 35-5' and slightly less than that of 'Ctr 4-10'. 'JSC 2-21-18' leaves are slightly convex, sparsely hirsute on the abaxial and adaxial surfaces, and smooth on the edges. Hairs on the leaves attain a maximum length of approximately 1 mm. Leaves emanating from the last visible node below the apex of shoots vary in width at their base from 2 to 4 mm and attain a length from about 25 to 38 mm. The ligule is a membranous rim about 0.2 mm long with short hairs on the edge except at the outer edges that have much longer hairs. Leaf sheaths are glabrous.

Figure 3:
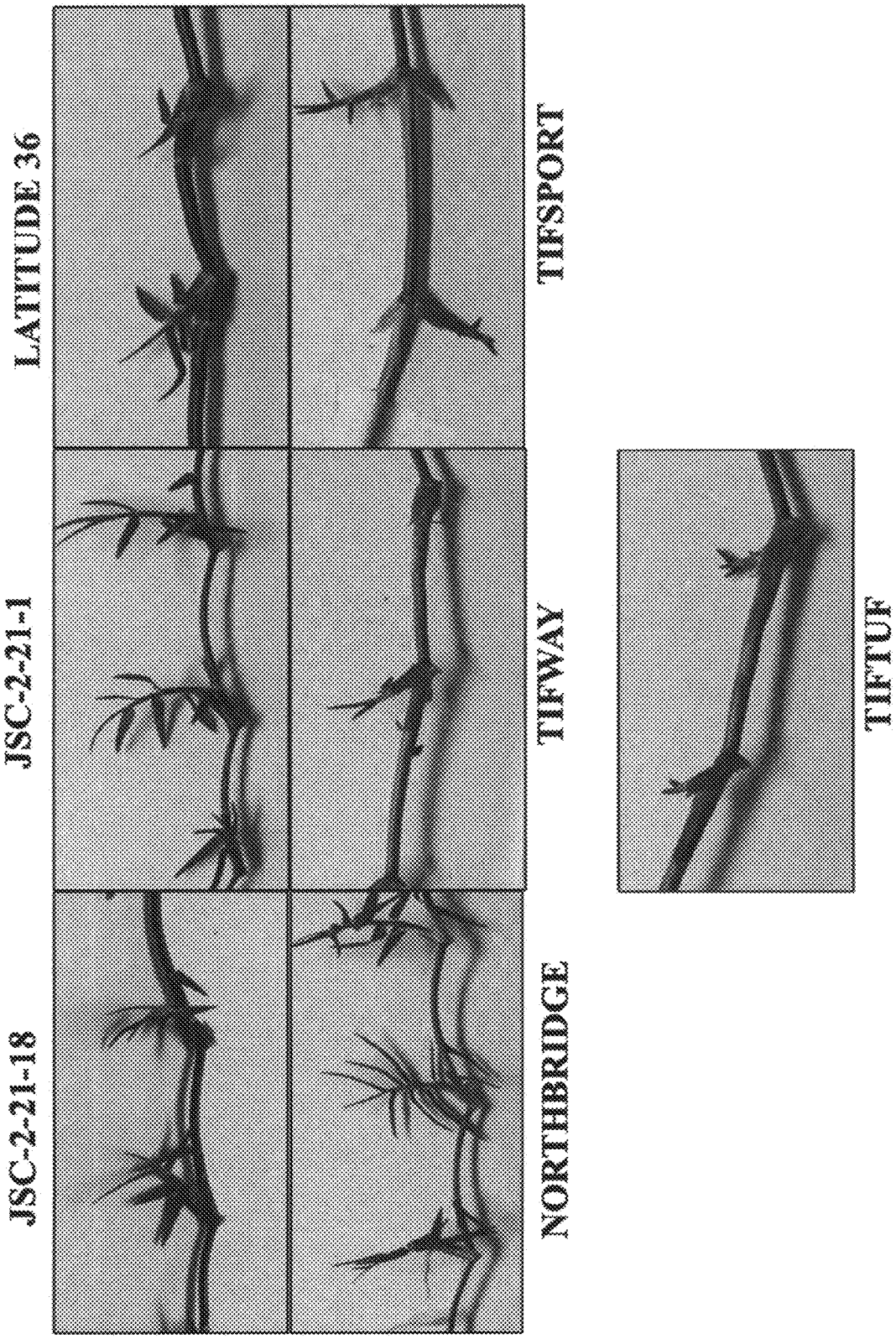
FIG. 3 shows a stolon internode of 'JSC 2-21-18' in comparison to stolon internodes of other turf bermudagrass cultivars.

'JSC 2-21-18' stolons are slender with internodes attaining maximum diameter and length of approximately 1 mm and 20 mm, respectively (Table 1). A stolon internode of 'JSC 2-2-18' in comparison to internodes of other turf bermudagrass cultivars are shown in FIG. 3. 'JSC 2-21-18' stolon internodes periodically accumulate anthocyanin pigment in response to environmental conditions and/or developmental stages. The pigment typically results in reddish purple color of the 'JSC 2-21-18' stolon internodes that may vary in intensity through time and growth stages. When assessed on Jun. 26, 2018, 'JSC 2-21-18' internodes were reddish purple in color corresponding to Munsell color 5R 3/4 (Table 1). The color of 'JSC 2-21-18' stolon internodes was judged identical to those of 'JSC 2-21-1' and 'Latitude 36' and only slightly lighter in reddish purple shade than 'Northbridge' stolon internodes which had color corresponding to Munsell color 5R 4/4 (Table 1). Stolon internodes of 'Tifway', 'TifSport' and 'TifTuf' were green in color corresponding to Munsell colors 2.5GY 5/4, 2.5GY 5/4, and 2/5GY 6/6, respectively (FIG. 3, Table 1).

Figure 4:
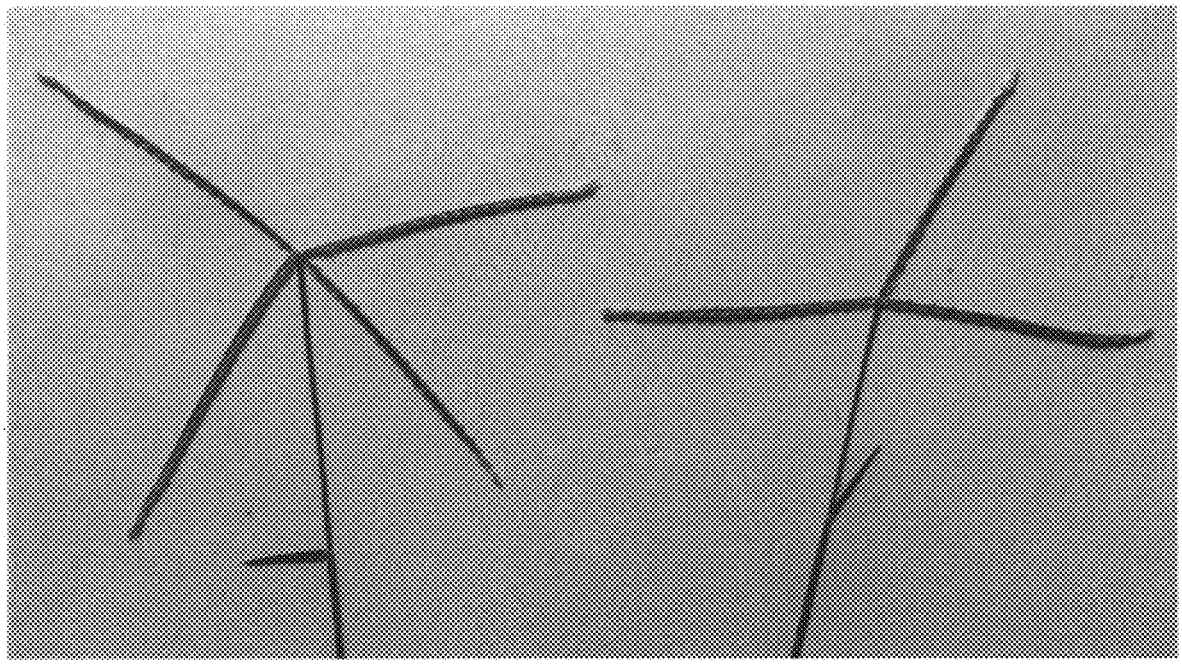
FIG. 4 is a photo of an inflorescence of 'JSC 2-21-18' turf bermudagrass.
Figure 5:
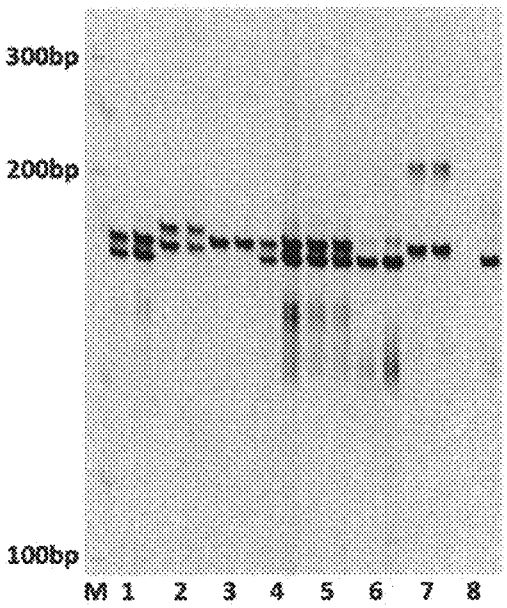
FIG. 5 shows DNA bands amplified in 'JSC 2-21-18' in comparison to seven other clonal turf bermudagrass cultivars by the SSR primer pair CDCA2-181/182. DNA bands were amplified by the SSR primer pair CDCA2-181/182 in eight clonal bermudagrass genotypes: 1. JSC 2-20-14; 2. JSC 2-21-1; 3. JSC 2-21-18; 4. Latitude 36; 5. Northbridge; 6. Tifway; 7. Tahoma 31; 8. TifTuf. M, 50-1500 bp DNA sizing standard (LI-COR).
Figure 6:
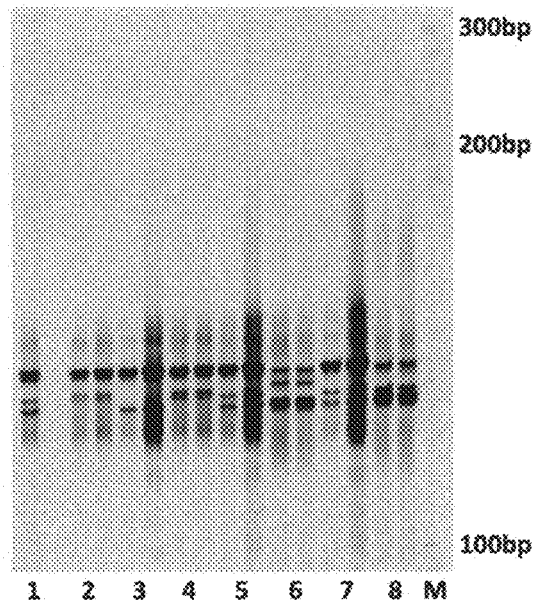
FIG. 6 shows DNA bands amplified in 'JSC 2-21-18' in comparison to seven other clonal turf bermudagrass cultivars by the SSR primer pair CDCA7-615/616. DNA bands were amplified by the SSR primer pair CDCA7-615/616 in eight clonal bermudagrass genotypes: 1. JSC 2-20-14; 2. JSC 2-21-1; 3. JSC 2-21-18; 4. Latitude 36; 5. Northbridge; 6. Tifway; 7. Tahoma 31; 8. TifTuf. M, 50-1500 bp DNA sizing standard (LI-COR).
Figure 7:
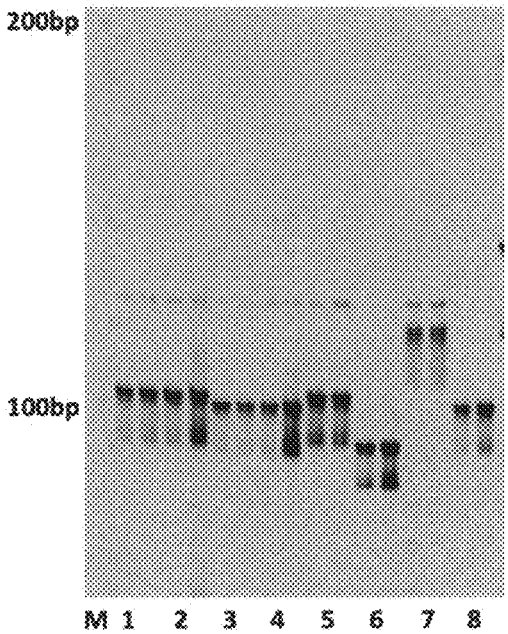
FIG. 7 shows DNA bands amplified in 'JSC 2-21-18' in comparison to seven other clonal turf bermudagrass cultivars by the SSR primer pair CDGA2-1021/1022. DNA bands were amplified by the SSR primer pair CDGA2-1021/1022 in eight clonal bermudagrass genotypes: 1. JSC 2-20-14; 2. JSC 2-21-1; 3. JSC 2-21-18; 4. Latitude 36; 5. Northbridge; 6. Tifway; 7. Tahoma 31; 8. TifTuf. M, 50-1500 bp DNA sizing standard (LI-COR).
Figure 8:
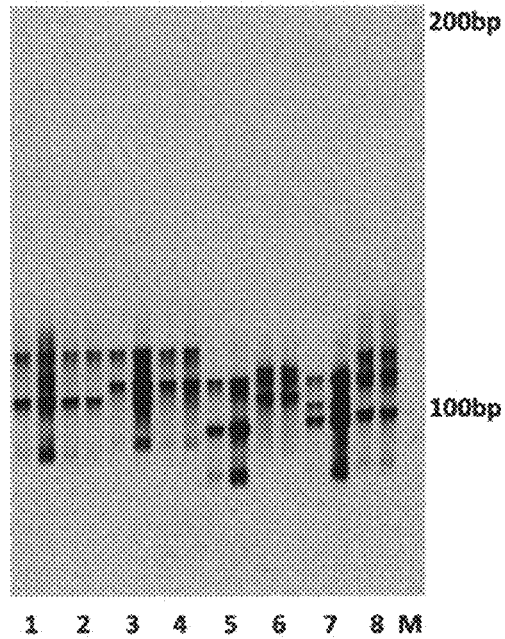
FIG. 8 shows DNA bands amplified in 'JSC 2-21-18' in comparison to seven other clonal turf bermudagrass cultivars by the SSR primer pair CDGA8-1783/1784. DNA bands were amplified by the SSR primer pair CDGA8-1783/1784 in eight clonal bermudagrass genotypes: 1. JSC 2-20-14; 2. JSC 2-21-1; 3. JSC 2-21-18; 4. Latitude 36; 5. Northbridge; 6. Tifway; 7. Tahoma 31; 8. TifTuf. M, 50-1500 bp DNA sizing standard (LI-COR).

Inflorescences typically have three or four racemes arranged in a single whorl with the latter occurring at a greater frequency than the former. FIG. 4 shows two inflorescences with three and four racemes, respectively, arranged in a single whorl. 'Cda 35-5' and 'Ctr 4-10' parents typically have four and three racemes, respectively, arranged in a single whorl. Racemes of 'JSC 2-21-18' typically contain about 30 spikelets spaced about 1 mm apart and being approximately 2 mm in length. The lower and upper glumes of spikelets are respectively approximately ½ and ⅝ the length of the spikelet. Stigma color is purple. Anther color is yellow with light purple tips. Anthers contain few, or no, viable pollen grains.

FIGS. 5-8 show DNA profiles of 'JSC 2-21-18' in comparison to seven other clonal turf bermudagrass cultivars. The profiles were generated using four simple sequence repeat (SSR) primer pairs. Each DNA sample had two replicates in PCR. The numbers at the bottom of each figure code for cultivars as follows: 1='JSC 2-20-14', 2='JSC 2-21-1', 3='JSC 2-21-18', 4='Latitude 36', 5='Northbridge', 6='Tifway', 7='Tahoma 31', and 8='TifTuf'. Each code number is centered below the two replicate profiles of each cultivar for each primer pair. SSR primer pairs CDCA2-181/182 (FIG. 5) and CDCA7-615/616 (FIG. 6) differentiates 'JSC 2-21-18' from each of the other seven cultivars. The SSR primer pair CDGA2-1021/1022 (FIG. 7) differentiates 'JSC 2-21-18' from all cultivars except 'Latitude 36' and 'TifTuf'. Primer pair CDGA8-1783/1784 (FIG.

8) differentiates 'JSC 2-21-18' from all cultivars except 'Latitude 36'. Accordingly, the combined SSR profiles confirm the genetic distinctness of 'JSC 2-21-18' in comparison to the other seven cultivars.

Characteristics and Performance

Replicated small plot testing initiated in 2010 by JSC indicated 'JSC 2-21-18' to have overall performance equal to or better than industry standard cultivars included in the test. Specifically, 'JSC 2-21-18' was indicated to be well adapted to the Enid, Okla. (36° 24'2"N 97° 52'51"W) test site and consistently high in visual turf quality. Its good adaptation was evidenced by the absence of winter injury and early green-up in the growing season. Characteristics contributing to its high visual turf quality included fine texture, high shoot density resulting in a uniformly dense sod, and acceptable green color.

Based on JSC test results, 'JSC 2-21-18' was entered in the NTEP 2013 bermudagrass test. The 2013 NTEP bermudagrass test was conducted at 19 test sites in the central and southern United States. The test contained 35 entries encompassing 17 clonal and 18 seed propagated cultivars. The number of test sites reporting data for Progress Reports NTEP 15-2 (2013-14), 16-6 (2015), 17-6 (2016) and 18-12 (2017) were 17, 19, 19, and 19, respectively. NTEP No. 18-14, released in December 2018, is the final report for the 2013 test. Details of the test and test results are available at www.ntep.org.

Data from NTEP testing supported JSC data indicating overall high performance of 'JSC 2-21-18'. Tables 2 through 11 contain data extracted from NTEP Reports for commercial clonal cultivars in the test. The top performing entries in the NTEP test for turf quality and many other traits were clotial cultivars. The high visual turf quality of 'JSC 2-21-18' is evidenced by the results in Table 2. 'JSC 2-21-18' had mean visual turf quality ratings (TQR) significantly higher than or equal to those of all clonal cultivars except 'TifTuf' in 2017. 'JSC 2-21-18' had significantly higher TQU than those of 'Astro' in all test years and for the overall mean. The TQR of 'JSC 2-21-18' was significantly higher than those of 'Patriot' and 'Celebration' in three and four of the test years, respectively, and for the overall mean. The TQR of 'JSC 2012-18' was significantly higher than those of 'Tifway' in 2014 and 2015. 'JSC 2-21-18' TQR (all quality ratings from all locations) were in the top 25% of all entries (35 entries) for 80% of the locations, indicating stable performance over locations and years.

'JSC 2-21-18' had mean leaf texture ratings (LTR) higher than or equal to all commercial cultivars in the test (Table 3). The LTR for 'JSC 2-21-18', 'Latitude 36', and 'Tahoma 31' were uniformly high (indicating fine texture) and not statistically different. 'JSC 2-21-18' had LTR significantly higher than those of 'Patriot', 'Celebration', and 'Astro' in all test years and for the 4-year mean. 'JSC 2-21-18' had significantly higher ratings than 'Tifway', a long-time industry standard cultivar, for all years except 2017. The LTR of 'JSC 2-21-18' were significantly higher than those for 'TifTuf' in 2013-14 and 2015.

Mean NTEP genetic color ratings (GCR) indicate 'JSC 2-21-18' to have lighter green color compared to some cultivars in the test (Table 4). 'Patriot' had significantly higher GCR than those of 'JSC 2-21-18' for each of the four years and for the overall mean. 'Tahoma 31' had significantly higher GCR than those of 'JSC 2-21-18' each of the four test years, but not for the overall mean. 'Tifway' and 'Celebration' had significantly higher GCR than those of 'JSC 2-21-18' for three of four years. 'TifTuf' and 'Latitude 36' had significantly higher GCR than those of 'JSC 2-21-18' in two and one test years, respectively. 'JSC 2-21-18' had significantly higher GCR only from those of 'Astro' in 2015. The indicated lighter green color of 'JSC 2-21-18' compared to top rated cultivars for this trait is not expected to limit its use. 'JSC 2-21-18' is similar in color to 'Latitude 36', a popular widely-used cultivar.

None of the clonal cultivars had mean NTEP spring green-up ratings (SGR) significantly higher than those of 'JSC 2-21-18' in any test year (Table 5). The SGR of 'JSC 2-21-18' were significantly higher than those of 'Tifway', 'Patriot', and 'Celebration' in three of the four years and were significantly higher than those of 'Tifway' and 'Celebraton' for the overall mean. The SGR of 'JSC 2-21-18' were significantly higher than those of 'Latitude 36' and 'Astro' in 2014 and 2015 and were significantly higher than those of 'TifTuf' in 2014. Spring green-up is related to winterhardiness conditioned by tolerance to freezing temperatures. Accordingly, the spring green-up ratings of 'JSC 2-21-18' indicate it to be sufficiently winterhardy for use in the norther region of the USA where bermudagrass has traditionally been grown.

Mean NTEP stand density ratings (SDR) for spring, summer and fall are shown in Tables 6, 7 and 8, respectively. Only 'TifTuf' in 2017 had a significantly higher spring SDR than that of 'JSC 2-21-18' (Table 6). 'JSC 2-21-18' had significantly higher spring SDR than those of 'Patriot', 'Celebration', and 'Astro' for two of the four test years and for the overall mean. 'JSC 2-21-18' had significantly higher spring SDR than that of 'Tahoma 31' in 2014. None of the cultivars had summer SDR significantly higher than those of 'JSC 2-21-18' (Table 7). 'JSC 2-21-18' had summer SDR significantly higher than those of 'Celebration' in each of the test years and for the overall mean. The summer SDR for 'JSC 2-21-18' were significantly higher than those of 'Patriot' and 'Astro' in two and three of the four test years, respectively, and for the overall mean. The summer SDR for 'JSC 2-21-18' was higher than that of 'Tifway' in 2014. None of the cultivars had fall SDR significantly higher than those of 'JSC 2-21-18' in any test year or for the overall mean (Table 8). 'JSC 2-21-18' had significantly higher fall SDR than those of 'Astro' in three of the four test years and for the overall mean. 'JSC 2-21-18' fall SDR were significantly higher than those of 'Patriot' in two of the test years and for the overall mean, and significantly higher than those of 'Celebration' in 2016. The SDR data indicate 'JSC 2-21-18' to maintain a dense stand throughout the growing season that is better than or equal to other clonal cultivars in the test.

Mean NTEP percent living ground cover ratings (PLGCR) for spring, summer, and fall are in Tables 9, 10, and 11, respectively. The spring PLGCR for 'JSC 2-21-18' were significantly higher than or equal to those of all other cultivars (Table 9). 'JSC 2-21-18' had significantly higher spring PLGCR than those of 'Celebration' in all test years and for the overall mean. Spring PLGCR for 'JSC 2-21-18' was significantly higher than those of 'Tifway' in two of the test years and for the overall mean. 'JSC 2-21-18' spring PLGCR were higher than those of 'Latitude 36' and 'Patriot' in two of the test years. Only 'TifTuf' in 2017 and 'Astro' in 2016 had significantly higher summer PLGCR than those of '2-21-18' (Table 10). 'JSC 2-21-18' had significantly higher summer PLGCR than those of 'Latitude 36', 'Tifway', and 'Celebration' in two of the test years and for the overall mean. 'JSC 2-21-18' had significantly higher summer PLGCR than those of 'Patriot' in two test years. Fall PLGCR for 'Tahoma 31', 'TifTuf' and 'Tifway' were significantly higher than those of '2-21-18' in 2017 (Table 11). The fall PLGCR for '2-21-18' were significantly higher than those of 'Latitude 36', 'Tifway', and 'Celebration' in 2014 and 'Patriot' in 2016 and 2017. The PLGCR data indicate 'JSC 2-21-18' to maintain high levels of living ground cover through the growing season that are generally equal to or better than other commercial turfgrass cultivars.

Summary Comparative Performance

'JSC 2-21-18' is indicated by available test data to have overall performance equal to or better than current commercial clonal turf bermudagrass cultivars with which it has been compared. Data indicate it to be adapted throughout the traditional geographic region in the USA where turf bermudagrass is grown. Its good cold tolerance reduces risk of winter injury compared to many turf bermudagrass cultivars, particularly when grown in the region of transition between warm- and cool-season grass species. It has consistently demonstrated high visual turf quality due primarily to its very fine texture, good color, and maintenance of a uniform dense stand (sod) throughout the growing season.

TABLE 1

Stolon internode length, diameter and Munsell Color Chart ratings and leaf length and width of seven turf bermudagrass cultivars growing in greenhouse pots Jun. 26, 2018.[1]

| | Internode | | | Leaf | |
|---|---|---|---|---|---|
| Cultivar | Length | Diameter mm | Munsell[3] H V/C | Length | Width mm |
| JSC 2-21-1 | 29.25 ab[2] | 1.24 bc | 5R3/4 | 28.20 b | 1.57 c |
| JSC 2-21-18 | 24.76 ab | 1.06 c | 5R 3/4 | 20.02 b | 1.61 c |
| Latitude 36 | 25.81 ab | 1.15 bc | 5R 3/4 | 18.97 b | 1.66 bc |
| Northbridge | 30.54 a | 1.32 b | 5R 4/4 | 29.30 ab | 1.95 ab |
| Tifway | 24.40 ab | 1.30 a | 2.5 GY 5/4 | 39.23 a | 1.65 bc |
| Tifsport | 21.06 b | 1.34 b | 2.5 GY 5/4 | 21.06 b | 1.34 c |
| Tiftuf | 27.57 ab | 1.62 a | 2.5 GY 6/6 | 26.80 b | 2.04 a |
| Mean | 26.20 | 1.29 | | 26.23 | 1.69 |
| Statistical Sig.[4] | * | ** | | ** | ** |

[1]Each cultivar was grown in one 30 cm diameter pot in a greenhouse. Stolons of each cultivar were allowed to grow over the edges of the pots and attain lengths up to about 30 cm. Measurements were made on the 5th internode from the apex of ten respective stolons per cultivar. Leaf measurements were from leaves emanating from the subtending node, with length being from the collar to the apex and width being taken near the leaf base.
[2]Means in the same column followed by the same letter are not significantly different as indicated by Tukeys's Honest Significant Difference Test (P = 0.05).
[3]Munsell Color Charts for Plant Tissues, GretagMacbeth LLC, 617 Little Britain Road, New Windsor, NY 12553-6148. H V/C = Hue Value/Chroma
[4]*, ** Means are significantly different at the 0.05 and 0.01 probability levels, respectively.

TABLE 2

Turfgrass quality ratings and maximum in top 25 percent for 'JSC 2-21-18' and commercial vegetative cultivars in the National Turfgrass Evaluation Program (NTEP) 2013 bermudagrass test.

| | Year[1] | | | | | 5-Yr Summary[2] | |
|---|---|---|---|---|---|---|---|
| Cultivar | 2013 | 2014 | 2015 | 2016 | 2017 | Mean | Maximum[3] |
| | Turfgrass quality ratings 1-9, 9 = ideal turf | | | | | | |
| TifTuf (DT-1) | 6.5 | 6.6 | 6.7 | 6.8 | 6.9 | 6.7 | 93.3 |
| JSC 2-21-18 | 6.2 | 6.5 | 6.7 | 6.6 | 6.6 | 6.6 | 80.0 |

TABLE 2-continued

Turfgrass quality ratings and maximum in top 25 percent for 'JSC 2-21-18' and commercial vegetative cultivars in the National Turfgrass Evaluation Program (NTEP) 2013 bermudagrass test.

| | Year[1] | | | | | 5-Yr Summary[2] | |
|---|---|---|---|---|---|---|---|
| Cultivar | 2013 | 2014 | 2015 | 2016 | 2017 | Mean | Maximum[3] |
| | Turfgrass quality ratings 1-9, 9 = ideal turf | | | | | | |
| Tahoma 31 (OKC 1131) | 6.5 | 6.5 | 6.6 | 6.6 | 6.8 | 6.6 | 73.3 |
| Latitude 36 | 6.3 | 6.4 | 6.3 | 6.7 | 6.7 | 6.6 | 66.7 |
| Tifway | 6.0 | 5.9 | 5.8 | 6.5 | 6.6 | 6.3 | 46.7 |
| Patriot | 5.9 | 6.0 | 6.1 | 6.3 | 6.3 | 6.2 | 46.7 |
| Astro | 5.8 | 5.8 | 6.0 | 6.2 | 6.0 | 6.0 | 6.7 |
| Celebration | 6.1 | 5.5 | 5.2 | 5.8 | 5.8 | 5.7 | 13.3 |
| LSD Value[4] | 0.3 | 0.2 | 0.2 | 0.2 | 0.2 | 0.3 | |
| C.V.[5] | 6.9 | 9.7 | 8.1 | 7.3 | 8.3 | 7.3 | |

[1]Data are from appendix tables in NTEP Progress Reports 15-2 (2013-2014), 16-6 (2015), 17-6 (2016), and 18-12(2017).
[2]Data are from the appendix table in NTEP Final Report 18-4.
[3]The percentage of locations where that entry finished in the top 25% of all entries (35 total entries).
[4]To determine statistical differences among cultivars within a column, subtract one entry's mean from another entry's mean. Statistical difference occurs when this value is larger than the corresponding Least Significant Difference (LSD 0.05) value.
[5]C. V. (coefficient of variation) indicates the percent variation of the mean in each column.

TABLE 3

Leaf texture ratings for 'JSC 2-21-18' and commercial vegetative bermudagrass cultivars in the National Turfgrass Evaluation Program (NTEP) 2013 bermudagrass test.

| | Year[1] | | | | |
|---|---|---|---|---|---|
| Cultivar | 2013-14 | 2015 | 2016 | 2017 | Mean[2] |
| | Leaf texture ratings 1-9, 9 = very fine | | | | |
| Latitude 36 | 7.6 | 6.7 | 6.5 | 6.8 | 6.4 |
| JSC 2-21-18 | 7.7 | 6.8 | 6.5 | 6.7 | 6.1 |
| Tahoma 31 (OKC 1131) | 7.4 | 6.5 | 6.4 | 6.7 | 6.1 |
| Tifway | 7.3 | 6.0 | 6.0 | 6.6 | 6.0 |
| TifTuf (DT-1) | 7.1 | 6.3 | 6.3 | 6.6 | 5.9 |
| Patriot | 6.5 | 6.0 | 5.6 | 5.7 | 5.2 |
| Astro | 6.2 | 5.5 | 5.2 | 5.6 | 5.1 |
| Celebration | 6.1 | 5.3 | 5.3 | 5.5 | 4.9 |
| LSD Value[3] | 0.3 | 0.3 | 0.4 | 0.3 | 0.5 |
| C.V.[4] | 8.7 | 9.4 | 10.7 | 8.7 | 11.7 |

[1]Data are from NTEP Progress Reports 15-2 (2013-2014), Table 11C ; 16-6 (2015), Table 22C; 17-6 (2016), Table 11C; and 18-12 (2017), Table 9C.
[2]Data are from Final Report NTEP No. 18-4, Table 9C.
[3]To determine statistical differences among cultivars within a column, subtract one entry's mean from another entry's mean. Statistical difference occurs when this value is larger than the corresponding Least Significant Difference (LSD 0.05) value.
[4]C.V. (coefficient of variation) indicates the percent variation of the mean in each column.

TABLE 4

Genetic color ratings for 'JSC 2-21-18' and commercial vegetative bermudagrass cultivars in the National Turfgrass Evaluation Program (NTEP) 2013 bermudagrass test.

| | Year[1] | | | | |
|---|---|---|---|---|---|
| Cultivar | 2014 | 2015 | 2016 | 2017 | Mean[2] |
| | Genetic color ratings 1-9, 9 = dark green | | | | |
| Patriot | 7.4 | 7.2 | 7.7 | 7.5 | 7.4 |
| Celebration | 7.7 | 6.6 | 7.2 | 7.3 | 7.1 |
| Tifway | 7.6 | 6.7 | 7.4 | 6.8 | 7.1 |
| Tahoma 31 (OKC 1131) | 7.2 | 7.1 | 7.1 | 6.7 | 6.9 |
| JSC 2-21-18 | 6.6 | 6.4 | 6.5 | 6.1 | 6.7 |
| TifTuf (DT-1) | 7.1 | 6.6 | 6.9 | 6.2 | 6.7 |

TABLE 4-continued

Genetic color ratings for 'JSC 2-21-18' and commercial vegetative bermudagrass cultivars in the National Turfgrass Evaluation Program (NTEP) 2013 bermudagrass test.

| | Year[1] | | | | |
|---|---|---|---|---|---|
| | 2014 | 2015 | 2016 | 2017 | Mean[2] |
| Cultivar | Genetic color ratings 1-9, 9 = dark green | | | | |
| Latitude 36 | 7.1 | 6.7 | 6.7 | 6.4 | 6.6 |
| Astro | 6.3 | 5.7 | 6.2 | 5.9 | 6.3 |
| LSD Value[3] | 0.3 | 0.4 | 0.3 | 0.3 | 0.5 |
| C.V.[4] | 10.1 | 13.7 | 8.3 | 10.7 | 10.7 |

[1]Data are from NTEP Progress Reports 15-2 (2013-2014), Table 9C; 16-6 (2015), Table 20C; 17-6 (2016), Table 9C; and 18-12 (2017), Table 7C.
[2]Data are from Final Report NTEP No. 18-4, Table 7C.
[3]To determine statistical differences among cultivars within a column, subtract one entry's mean from another entry's mean. Statistical difference occurs when this value is larger than the corresponding Least Significant Difference (LSD 0.05) value.
[4]C.V. (coefficient of variation) indicates the percent variation of the mean in each column.

TABLE 5

Spring green-up ratings for 'JSC 2-21-18' and commercial vegetative bermudagrass cultivars in the National Turfgrass Evaluation Program (NTEP) 2013 bermudagrass test.

| | Year[1] | | | | |
|---|---|---|---|---|---|
| | 2014 | 2015 | 2016 | 2017 | Mean[2] |
| Cultivar | Spring green-up ratings 1-9, 9 = completely green | | | | |
| Tahoma 31 (OKC 1131) | 6.1 | 6.0 | 5.3 | 6.0 | 5.7 |
| Astro | 5.1 | 5.4 | 5.6 | 5.7 | 5.5 |
| JSC 2-21-18 | 5.8 | 6.0 | 5.3 | 6.1 | 5.3 |
| TifTuf (DT-1) | 5.2 | 5.6 | 5.3 | 6.1 | 5.3 |
| Latitude 36 | 5.3 | 5.4 | 5.5 | 6.0 | 4.9 |
| Patriot | 4.8 | 4.5 | 4.9 | 5.2 | 4.8 |
| Tifway | 4.1 | 4.7 | 4.8 | 5.3 | 4.5 |
| Celebration | 3.7 | 4.5 | 4.9 | 4.7 | 4.4 |
| LSD Value[3] | 0.4 | 0.5 | 0.5 | 0.5 | 0.7 |
| C.V.[4] | 18.5 | 19.9 | 17.6 | 18.1 | 20.8 |

[1]Data are from NTEP Progress Reports 15-2 (2013-2014), Table 10C; 16-6 (2015), Table 21C; 17-6 (2016), Table 10C; and 18-12 (2017), Table 8C.
[2]Data are from Final Report NTEP No. 18-4, Table 8C.
3To determine statistical differences among cultivars within a column, subtract one entry's mean from another entry's mean. Statistical difference occurs when this value is larger than the corresponding Least Significant Difference (LSD 0.05) value.
[4]C.V. (coefficient of variation) indicates the percent variation of the mean in each column.

TABLE 6

Spring density ratings for 'JSC 2-21-18' and commercial vegetative bermudagrass cultivars in the National Turfgrass Evaluation Program (NTEP) 2013 bermudagrass test.

| | Year[1] | | | | |
|---|---|---|---|---|---|
| | 2014 | 2015 | 2016 | 2017 | Mean[2] |
| Cultivar | Spring density ratings 1-9, 9 = maximum density | | | | |
| JSC 2-21-18 | 7.0 | 7.3 | 6.2 | 6.0 | 6.8 |
| TifTuf (DT-1) | 7.1 | 6.9 | 5.8 | 6.9 | 6.8 |
| Latitude 36 | 7.0 | 6.8 | 6.7 | 6.2 | 6.8 |
| Tifway | 6.9 | 6.8 | 5.8 | 6.1 | 6.6 |
| Tahoma 31 (OKC 1131) | 6.3 | 7.1 | 5.7 | 5.9 | 6.4 |
| Patriot | 6.3 | 6.3 | 6.2 | 5.6 | 6.1 |
| Astro | 6.3 | 6.3 | 6.0 | 5.6 | 6.1 |
| Celebration | 6.6 | 5.5 | 4.8 | 6.0 | 6.0 |

TABLE 6-continued

Spring density ratings for 'JSC 2-21-18' and commercial vegetative bermudagrass cultivars in the National Turfgrass Evaluation Program (NTEP) 2013 bermudagrass test.

| | Year[1] | | | | |
|---|---|---|---|---|---|
| | 2014 | 2015 | 2016 | 2017 | Mean[2] |
| Cultivar | Spring density ratings 1-9, 9 = maximum density | | | | |
| LSD Value[3] | 0.6 | 0.5 | 0.9 | 0.8 | 0.6 |
| C.V.[4] | 9.4 | 10.4 | 13.9 | 14.2 | 11.9 |

[1]Data are from NTEP Progress Reports 15-2 (2013-2014), Table 13C; 16-6 (2015), Table 23C; 17-6 (2016), Table 12C; and 18-12 (2017), Table 10C.
[2]Data are from Final Report NTEP No. 18-4, Table 11C.
[3]To determine statistical differences among cultivars within a column, subtract one entry's mean from another entry's mean. Statistical difference occurs when this value is larger than the corresponding Least Significant Difference (LSD 0.05) value.
[4]C.V. (coefficient of variation) indicates the percent variation of the mean in each column.

TABLE 7

Summer density ratings for 'JSC 2-21-18' and commercial vegetative bermudagrass cultivars in the National Turfgrass Evaluation Program (NTEP) 2013 bermudagrass test.

| | Year[1] | | | | |
|---|---|---|---|---|---|
| | 2014 | 2015 | 2016 | 2017 | Mean[2] |
| Cultivar | Summer density ratings 1-9, 9 = maximum density | | | | |
| Latitude 36 | 7.6 | 7.3 | 6.8 | 7.3 | 7.4 |
| TifTuf (DT-1) | 7.7 | 7.4 | 6.9 | 7.4 | 7.4 |
| Tahoma 31 (OKC 1131) | 7.5 | 7.2 | 7.0 | 7.3 | 7.4 |
| JSC 2-21-18 | 7.7 | 7.3 | 7.1 | 6.9 | 7.3 |
| Tifway | 7.2 | 7.1 | 7.1 | 7.1 | 7.2 |
| Patriot | 6.9 | 6.7 | 6.6 | 6.4 | 6.7 |
| Celebration | 6.3 | 6.3 | 6.3 | 6.5 | 6.5 |
| Astro | 6.5 | 6.5 | 6.7 | 6.2 | 6.5 |
| LSD Value[3] | 0.4 | 0.4 | 0.5 | 0.5 | 0.4 |
| C.V.[4] | 8.3 | 7.3 | 10.5 | 10.4 | 9.1 |

[1]Data are from NTEP Progress Reports 15-2 (2013-2014), Table 14C; 16-6 (2015), Table 24C; 17-6 (2016), Table 13C; and 18-12 (2017), Table 11C.
[2]Data are from Final Report NTEP No. 18-4, Table 12C.
[3]To determine statistical differences among cultivars within a column, subtract one entry's mean from another entry's mean. Statistical difference occurs when this value is larger than the corresponding Least Significant Difference (LSD 0.05) value.
[4]C.V. (coefficient of variation) indicates the percent variation of the mean in each column.

TABLE 8

Fall density ratings for 'JSC 2-21-18' and commercial vegetative bermudagrass cultivars in the National Turfgrass Evaluation Program (NTEP) 2013 bermudagrass test.

| | Year[1] | | | | |
|---|---|---|---|---|---|
| | 2014 | 2015 | 2016 | 2017 | Mean[2] |
| Cultivar | Fall density rating is 1-9, 9 = maximum density | | | | |
| TifTuf (DT-1) | 7.7 | 7.3 | 7.8 | 7.5 | 7.6 |
| Tifway | 7.4 | 7.1 | 7.2 | 7.4 | 7.3 |
| Latitude 36 | 7.5 | 7.3 | 7.0 | 7.1 | 7.3 |
| JSC 2-21-18 | 7.5 | 7.2 | 7.5 | 7.1 | 7.3 |
| Tahoma 31 (OKC 1131) | 7.7 | 7.3 | 6.7 | 7.3 | 7.3 |
| Celebration | 7.1 | 6.9 | 6.3 | 6.7 | 6.8 |
| Astro | 6.4 | 6.5 | 6.5 | 6.5 | 6.5 |
| Patriot | 6.8 | 6.7 | 7.0 | 5.9 | 6.4 |

TABLE 8-continued

Fall density ratings for 'JSC 2-21-18' and commercial vegetative bermudagrass cultivars in the National Turfgrass Evaluation Program (NTEP) 2013 bermudagrass test.

| | Year[1] | | | | |
|---|---|---|---|---|---|
| | 2014 | 2015 | 2016 | 2017 | Mean[2] |
| Cultivar | Fall density rating is 1-9, 9 = maximum density | | | | |
| LSD Value[3] | 0.5 | 0.5 | 0.8 | 0.6 | 0.6 |
| C.V.[4] | 8.8 | 10.2 | 10.5 | 12.6 | 10.8 |

[1]Data are from NTEP Progress Reports 15-2 (2013-2014), Table 15C; 16-6 (2015), Table 25C; 17-6 (2016), Table 14C; and 18-12 (2017), Table 12C.

[2]Data are from Final Report NTEP No. 18-4, Table 13C.

[3]To determine statistical differences among cultivars within a column, subtract one entry's mean from another entry's mean. Statistical difference occurs when this value is larger than the corresponding Least Significant Difference (LSD 0.05) value.

[4]C.V. (coefficient of variation) indicates the percent variation of the mean in each column.

TABLE 9

Percent living ground cover ratings (spring) for 'JSC 2-21-18' and commercial vegetative bermudagrass cultivars in the National Turfgrass Evaluation Program (NTEP) 2013 bermudagrass test.

| | Year[1] | | | | |
|---|---|---|---|---|---|
| | 2014 | 2015 | 2016 | 2017 | Mean[2] |
| Cultivar | % ground cover rating | | | | |
| Tahoma 31 (OKC 1131) | 79.9 | 89.2 | 95.5 | 89.4 | 88.0 |
| JSC 2-21-18 | 73.7 | 91.1 | 96.9 | 88.7 | 87.6 |
| TifTuf (DT-1) | 70.6 | 87.9 | 95.3 | 92.4 | 86.6 |
| Astro | 68.6 | 84.9 | 95.2 | 89.6 | 83.6 |
| Latitude 36 | 58.2 | 78.3 | 96.4 | 90.5 | 80.7 |
| Patriot | 70.2 | 79.5 | 92.3 | 81.1 | 80.4 |
| Tifway | 56.1 | 68.8 | 93.8 | 86.6 | 77.9 |
| Celebration | 59.8 | 66.6 | 85.3 | 79.1 | 75.0 |
| LSD Value[3] | 9.5 | 8.0 | 4.9 | 4.9 | 7.8 |
| C.V.[4] | 24.4 | 16.1 | 6.6 | 8.4 | 13.6 |

[1]Data are from NTEP Progress Reports 15-2 (2013-2014), Table 16C; 16-6 (2015), Table 26C; 17-6 (2016), Table 15C; and 18-12 (2017), Table 13C.

[2]Data are from Final Report NTEP No. 18-4, Table 14C.

[3]To determine statistical differences among cultivars within a column, subtract one entry's mean from another entry's mean. Statistical difference occurs when this value is larger than the corresponding Least Significant Difference (LSD 0.05) value.

[4]C.V. (coefficient of variation) indicates the percent variation of the mean in each column.

TABLE 10

Percent living ground cover ratings (summer) for 'JSC 2-21-18' and commercial vegetative bermudagrass cultivars in the National Turfgrass Evaluation Program 2013 bermudagrass test.

| | Year[1] | | | | |
|---|---|---|---|---|---|
| | 2014 | 2015 | 2016 | 2017 | Mean[2] |
| Cultivar | % ground cover rating | | | | |
| TifTuf (DT-1) | 89.9 | 96.9 | 95.9 | 97.0 | 95.3 |
| Tahoma 31 (OKC 1131) | 90.1 | 96.6 | 95.9 | 93.5 | 94.7 |
| Astro | 89.1 | 96.1 | 97.3 | 91.4 | 94.3 |
| JSC 2-21-18 | 89.5 | 96.8 | 94.7 | 93.3 | 94.2 |
| Patriot | 82.4 | 92.1 | 91.3 | 92.5 | 90.6 |
| Latitude 36 | 72.9 | 84.5 | 95.2 | 95.4 | 88.9 |
| Tifway | 76.2 | 78.4 | 95.8 | 96.1 | 88.8 |
| Celebration | 75.6 | 77.8 | 95.8 | 94.4 | 88.3 |
| LSD Value[3] | 5.8 | 6.0 | 2.4 | 3.4 | 4.2 |
| C.V.[4] | 10.9 | 9.5 | 3.2 | 5.0 | 6.1 |

[1]Data are from NTEP Progress Reports 15-2 (2013-2014), Table 17C; 16-6 (2015), Table 27C; 17-6 (2016), Table 16C; and 18-12 (2017), Table 14C.

[2]Data are from Final Report NTEP No. 18-4, Table 15C.

[3]To determine statistical differences among cultivars within a column, subtract one entry's mean from another entry's mean. Statistical difference occurs when this value is larger than the corresponding Least Significant Difference (LSD 0.05) value.

[4]C.V. (coefficient of variation) indicates the percent variation of the mean in each column.

TABLE 11

Percent living ground cover ratings (fall) for 'JSC 2-21-18* and commercial vegetative bermudagrass cultivars in the National Turfgrass Evaluation Program 2013 bermudagrass test.

| | Year[1] | | | | |
|---|---|---|---|---|---|
| | 2014 | 2015 | 2016 | 2017 | Mean[2] |
| Cultivar | % ground cover rating | | | | |
| Astro | 96.2 | 98.8 | 96.3 | 91.3 | 95.1 |
| TifTuf (DT-1) | 95.1 | 98.8 | 95.9 | 94.6 | 95.1 |
| JSC 2-21-18 | 97.0 | 98.6 | 96.5 | 89.1 | 94.8 |
| Tahoma 31 (OKC 1131) | 96.3 | 98.7 | 94.6 | 93.0 | 94.3 |
| Latitude 36 | 91.5 | 98.5 | 94.5 | 91.5 | 92.8 |
| Celebration | 84.9 | 98.5 | 95.4 | 91.4 | 92.2 |
| Patriot | 96.4 | 97.3 | 94.2 | 85.2 | 92.0 |
| Tifway | 81.2 | 98.4 | 94.4 | 94.0 | 91.0 |
| LSD Value[3] | 4.8 | 1.7 | 2.2 | 3.6 | 3.8 |
| C.V.[4] | 8.1 | 2.4 | 2.8 | 6.0 | 4.7 |

[1]Data are from NTEP Progress Reports 15-2 (2013-2014), Table 18C; 16-6 (2015), Table 28C; 17-6 (2016), Table 17C; and 18-12 (2017), Table 15C.

[2]Data are from Final Report NTEP No. 18-4, Table 16C.

[3]To determine statistical differences among cultivars within a column, subtract one entry's mean from another entry's mean. Statistical difference occurs when this value is larger than the corresponding Least Significant Difference (LSD 0.05) value.

[4]C.V. (coefficient of variation) indicates the percent variation of the mean in each column.

I claim:

1. A turf clonal bermudagrass cultivar substantially as described and illustrated in the specification herein.

* * * * *